United States Patent [19]

Schulte-Huermann

[11] Patent Number: 5,037,512

[45] Date of Patent: Aug. 6, 1991

[54] PROCESS FOR THE PURIFICATION OF BENZOIC ACID BY DISTILLATION WITH AN AMINE

[75] Inventor: Werner Schulte-Huermann, Krefeld, Fed. Rep. of Germany

[73] Assignee: Bayer Aktiengesellschaft, Leverkusen, Fed. Rep. of Germany

[21] Appl. No.: 395,229

[22] Filed: Aug. 17, 1989

Related U.S. Application Data

[63] Continuation of Ser. No. 736,502, May 21, 1985, abandoned.

[30] Foreign Application Priority Data

May 30, 1984 [DE] Fed. Rep. of Germany ....... 3420111

[51] Int. Cl.$^5$ .................. B01D 3/34; C07C 51/44; C07C 63/06
[52] U.S. Cl. ........................... 203/38; 203/51; 203/56; 203/59; 203/63; 203/71; 203/73; 203/77; 562/494; 562/863
[58] Field of Search ............... 203/38, 59, 63, 51, 203/56, 73, 77, 71; 562/494, 493, 863, 866

[56] References Cited

U.S. PATENT DOCUMENTS

| | | |
|---|---|---|
| 2,283,991 | 5/1942 | Hill ................... 562/494 |
| 2,568,095 | 9/1951 | Smith et al. ........... 562/494 |
| 2,865,959 | 12/1958 | Toland ................. 562/863 |
| 3,078,303 | 2/1963 | Sweeney ............... 562/494 |
| 3,115,521 | 12/1963 | Swakon ................ 562/494 |
| 3,159,673 | 12/1964 | Weil .................. 562/494 |
| 4,092,353 | 5/1978 | Wolf .................. 562/494 |
| 4,430,181 | 2/1984 | Neumann et al. ........ 562/859 |

FOREIGN PATENT DOCUMENTS 813888 5/1959 United Kingdom ............... 562/863

*Primary Examiner*—Wilbur Bascomb
*Attorney, Agent, or Firm*—Sprung Horn Kramer & Woods

[57] ABSTRACT

A process for the purification of crude benzoic acid obtained by the catalytic oxidation of toluene in the liquid phase, which is contaminated with impurities including phthalic acid and benzylbenzoate, the process involves distilling the crude benzoic acid in a first distillation in the presence of an aliphatic amine or a mixture of aliphatic amines of the formula $$HNR^1R^2$$

wherein
R$^1$ represents hydrogen or a straight-chain or branched hydroxyalkyl or aminoalkyl radical with 1 to 6 carbon atoms and
R$^2$ represents a straight-chain or branched hydroxyalkyl or aminoalkyl radical with 1 to 6 carbon atoms, and/or the salts of these amines, recovering from this distillation (a) a purified benzoic acid and (b) a benzylbenzoate containing residue, working up the residue by a second distillation and chlorinating the distillate resulting from this second distillation to give a benzoyl-chloride virtually free of benzonitrile.

16 Claims, No Drawings

PROCESS FOR THE PURIFICATION OF BENZOIC ACID BY DISTILLATION WITH AN AMINE

This is a continuation of application Ser. No. 06/736,502, filed May, 21, 1985, now abandoned.

The invention relates to a process for the purification of benzoic acid which has been obtained by catalytic oxidation of toluene with air in the liquid phase.

In the known processes for the preparation of benzoic acid by liquid phase oxidation of toluene with air in the presence of metal compounds as catalysts, for example cobalt compounds and manganese compounds, at elevated temperature, benzoic acid is formed which, inter alia, contains phthalic acid (compare Chem. Zentralbl. 1942, II page 2642) and relatively large amounts of benzyl benzoate as impurities (compare Ullmanns Encyclopadie der technischen Chemie [Ullmann's Encyclopaedia of Industrial Chemistry], 4th edition, Volume 8, pages 367 to 369, 1974). However, such impurities in general interfere with the further processing of the benzoic acid, in particular the further processing of the benzoic acid to sodium benzoate, which is as a rule obtained by a process in which a benzoic acid which has been purified by fractional distillation is dissolved in sodium hydroxide solution.

A sodium benzoate prepared in this manner is neither clearly soluble in ethanol, and does not correspond to the purity requirement according to the German Pharmacopoeia (DAB VII, 689–691 (1968)), nor soluble in ethylene glycol, which prohibits use in antifreezes. According to German Auslegeschrift 2,636,489, these disadvantages have been eliminated by adding small amounts of an amine, preferably ammonia, for the distillation of the crude benzoic acid, which means that the troublesome phthalic acid, the sodium salt of which is sparingly soluble in alcohol, is retained in the bottom product as a result of amidation or imidation and the excess ammonia is bonded as benzamide.

If, as is obvious for economic reasons, the distillation bottom product of the benzoic acid, which chiefly consists of benzyl benzoate and contains about 10% by weight of the benzoic acid employed, is to be worked up by distillation and utilised, for example by direct chlorination of the distillate obtained from the distillation bottom product to give benzoyl chloride (compare European Offenlegungschrift 78,993), the purification process described in German Auslegeschrift 2,636,489 is unsuitable, since the benzyl benzoate contained in the distillate still contains benzamide which is converted into benzonitrile on direct chlorination, so that a benzoyl chloride which has a benzonitrile content of up to 5% by weight and which cannot be utilised industrially is obtained. Working up of the distillation bottom product of the benzoic acid has therefore only been industrially appropriate and economically acceptable if at the same time the preparation of an alcohol-soluble sodium benzoate, as described above, was sacrificed.

A process has now been found for the purification of benzoic acid which has been obtained by catalytic oxidation of toluene with air in the liquid phase, which is characterised in that the distillation of the crude benzoic acid is carried out in the presence of aliphatic amines of the formula $HNR^1R^2$, wherein $R^1$ represents hydrogen or a straight-chain or branched hydroxyalkyl or aminoalkyl radical with 1 to 6 carbon atoms and $R^2$ represents a straight-chain or branched hydroxyalkyl or aminoalkyl radical with 1 to 6 carbon atoms, and/or salts thereof.

The preparation of benzoic acid by catalytic oxidation of toluene in the liquid phase can be carried out in the customary manner (compare Ullmanns Encyclopädie der technischen Chemie [Ullmann's Encyclopaedia of Industrial Chemistry], 4th edition, Volume 8, pages 367 to 369 (1974)). The excess toluene is usually separated off from the resulting benzoic acid by distillation. A benzoic acid pretreated in this manner can be used in the process according to the invention for further purification. It is also possible to use in the process according to the invention a benzoic acid which has already been crystallised or distilled. A benzoic acid containing up to 10% by weight, particularly preferably up to 8% by weight, of impurities is preferably employed in the process according to the invention.

Amines which are employed in the process according to the invention are those of the general formula $HNR^1R^2$, in which the radicals $R^1$ and $R^2$ have a straight-chain or branched hydroxyalkyl or aminoalkyl radical with 1 to 6 carbon atoms, preferably 2 or 3 carbon atoms. Examples of straight-chain or branched hydroxyalkyl and aminoalkyl radicals which may be mentioned are: 2-hydroxyethyl, 3-hydroxy-n-propyl, 2-hydroxy-iso-propyl, 4-hydroxy-n-butyl, 3-hydroxy-isobutyl, 2-hydroxy-tert.-butyl, 5-hydroxy-n-pentyl, 6-hydroxy-n-hexyl, 2-aminoethyl, 3-amino-n-propyl, 2-amino-iso-propyl, 4-amino-n-butyl, 3-amino-isobutyl, 2-amino-tert.-butyl, 5-amino-n-pentyl and 6-amino-n-hexyl radicals, preferably the 2-hydroxyethyl and the 2-aminoethyl radical.

Examples which may be mentioned of amines which, for reasons of appropriateness or cost, can be employed in the process according to the invention are β-aminoethanol, aminopropanol, amino-n-butanol, amino-sec.-butanol, amino-tert.-butanol, diethanolamine, dipropanolamine, ethylenediamine and diaminoethyleneamine, preferably β-aminoethanol and ethylenediamine. It is of course also possible to employ, besides the free amines, salts thereof, as long as these cause no interference in the further working up of the benzoic acid. Salts which can preferably be employed in the process according to the invention are those from acids which are highly volatile in comparison with benzoic acid, decompose without the formation of by-products and cause no corrosion. Examples of salts which may be mentioned are the carbonates, bicarbonates, formates, acetates, oxalates and benzoates, preferably the carbonates, bicarbonates and benzoates, of the abovementioned amines.

It is of course also possible to employ mixtures of the amines and/or their salts in the process according to the invention. In order to facilitate metering of relatively small amounts of amines, aqueous solutions of the amines can also be employed.

Small amounts of amines and/or salts thereof are adequate for the process according to the invention. The particular amount required depends above all on the quality of the benzoic acid formed during the toluene oxidation and can easily be determined by known analytical methods. However, it is in general sufficient to use the amine or its salts in amounts of about 0.01 to 0.001 mol, preferably 0.003 to 0.006 mol, per mol of benzoic acid.

However, it is of no significance for the process according to the invention if an excess of amine is employed. This may be advantageous if individual analyses are to be saved in the case of a batchwise procedure.

The process according to the invention can be carried out in a temperature range from about 80° to 250° C., preferably 120° to 230° C., and under pressures of 1 to 1013 mbar, preferably 10 to 600 mbar.

A particular embodiment of the process according to the invention comprises a procedure in which the benzoic acid formed during atmospheric oxidation of toluene in the presence of cobalt/manganese catalysts is freed from unreacted toluene by distillation, and a corresponding amine is added under the influence of heat, by stirring. The distillation of the benzoic acid can be carried out in a manner which is known per se in vacuo under about 18 mbar at a boiling point of about 140° C. After the first runnings have been removed, the pure product can be used for the preparation of sodium benzoate. The sodium benzoate prepared in this manner corresponds to the requirements of the German Pharmacopoeia and, since it is clearly soluble in ethylene glycol, can also be used in antifreezes.

The distillation bottom product of the benzoic acid can likewise be purified by distillation in a known manner in vacuo under about 4 mbar at a boiling point of about 160° to 170° C. A distillate which consists chiefly of benzyl benzoate and is virtually free from benzamide is obtained. If the benzyl benzoate prepared in this manner is subjected to direct chlorination, a highly pure benzoyl chloride which is virtually free from benzonitrile is formed.

The following examples serve to illustrate the process according to the invention. The crude benzoic acid used for these examples was prepared by atmospheric oxidation of toluene in the presence of cobalt/manganese salts at temperatures from 160° to 180° C. and was freed from toluene by heating to 190° C.

EXAMPLE 1

500 g of crude benzoic acid containing 0.25% by weight of phthalic anhydride were mixed with 0.50 g of ammonia (as 4.0 g of ammonium benzoate, 0.36 mol/-mol of phthalic acid) and the mixture was then distilled in vacuo over a 60 cm VA wire netting column. 448 f of benzoic acid containing 0.09% by weight of phthalic acid distilled over at an overhead temperature of 140° C. under a vacuum of 18 mbar. 10% strength aqueous sodium hydroxide solution was added to the distillate until the solution had a pH value of 7. The oil, consisting of byproducts, was removed and the aqueous phase was evaporated and, finally, dried in vacuo. 10 g of the sodium benzoate thus obtained were dissolved in 40 g of ethylene glycol, with stirring. A clear solution was formed.

The distillation residue (49 g), which predominantly consists of benzyl benzoate, was distilled over a Claisen attachment. Most of the residue (42 g) distilled over at an overhead temperature of 165° C. under a vacuum of 4 mbar. On the basis of analysis by gas chromatography, the distillate contained 2.51% by weight of benzamide and had an $N_2$ content of 0.35%.

EXAMPLES 2 to 7

Examples 2 to 7 were carried out by the procedure described in Example 1, using ammonia, as in the prior art, and the bifunctional amines according to the invention. The following table shows the result:

| Example No. | Addition of amine/ammonia mol/mol of phthalic acid | Amount in g | Solubility of the sodium benzoate in ethylene glycol | Phthalic acid content in % | Distillate of the residue Benzamide content % | $N_2$ content % |
|---|---|---|---|---|---|---|
| 2 | 5.0 ammonia | 0.71 | clear | 0.02 | 5.46 | 0.76 |
| 3 | 2.0 ammonia | 0.28 | slightly cloudy | 0.11 | 2.01 | 0.28 |
| 4 | 2.0 ethanolamine | 1.04 | clear | 0.08 | 0.01 | 0.02 |
| 5 | 3.6 ethanolamine | 1.86 | clear | <0.01 | 0.03 | 0.09 |
| 6 | 2.0 propanolamine | 1.21 | clear | <0.01 | 0.05 | 0.07 |
| 7 | 1.5 ethylenediamine | 0.73 | clear | <0.01 | 0.06 | 0.03 |

I claim:

1. A process for the purification of crude benzoic acid obtained by the catalytic oxidation of toluene in the liquid phase, which is contaminated with impurities including phthalic acid and benzylbenzoate, the process comprising distilling said crude benzoic acid in a first distillation in the presence of an aliphatic amine or a mixture of said amines of the formula $$HNR^1R^2,$$ 

wherein
  $R^1$ represents hydrogen or a straight-chain or branched hydroxyalkyl or aminoalkyl radical with 1 to 6 carbon atoms and
  $R^2$ represents a straight-chain or branched hydroxyalkyl or aminoalkyl radical with 1 to 6 carbon atoms, and/or salts thereof, recovering from this distillation (a) a purified benzoic acid and (b) a benzylbenzoate containing residue, working up said residue by a second distillation and chlorinating the distillate resulting from this second distillation to give a benzoylchloride virtually free of benzonitrile.

2. A process according to claim 1, wherein said amine is selected from the group consisting of beta-aminoethanol, aminopropanol, amino-n-butanol, amino-sec.-butanol, amino-tert.-butanol, diethanolamine, dipropanolamine, ethylenediamine, diaminoethyleneamine and mixtures thereof.

3. A process according to claim 1, wherein said amine is selected from the group consisting of beta-aminoethanol, ethylenediamine and mixtures thereof.

4. A process according to claim 1, wherein the amine is employed in amounts of 0.001 to 0.01 mol per mol of benzoic acid.

5. A process according to claim 1, wherein the amine is employed in amounts of 0.003 to 0.006 mol per mol of benzoic acid.

6. A process according to claim 1, wherein the first distillation is carried out at temperatures of 80° to 250° C.

7. A process according to claim 1, wherein the first distillation is carried out at a pressure of 1 to 1013 mbar.

8. A process according to claim 1, wherein the first distillation is carried out at a pressure of 10 to 600 mbar.

9. A process according to claim 1, wherein the first distillation is carried out at a temperature of 120° C. to 230° C.

10. A process according to claim 1, wherein said crude benzoic acid contains up to 10% by weight of impurities.

11. A process according to claim 1, wherein said crude benzoic acid contains up to 8% by weight of impurities.

12. A process according to claim 1, wherein said straight-chain or branched hydroxyalkyl or aminoalkyl radical has 2 to 3 carbon atoms.

13. A process according to claim 1, wherein $R^1$ is a radical selected from the group consisting of 2-hydroxyethyl, 3-hydroxy-n-propyl, 2-hydroxy-iso-propyl, 4-hydroxy-n-butyl, 3-hydroxy-isobutyl, 2-hydroxy-tert.-butyl, 5-hydroxy-n-pentyl, 6-hydroxy-n-hexyl, 2-aminoethyl, 3-amino-n-propyl, 2-amino-iso-propyl, 4-amino-n-butyl, 3-amino-isobutyl, 2-amino-tert.-butyl, 5-amino-n-pentyl and 6-amino-n-hexyl radicals.

14. A process according to claim 1, wherein $R^2$ is a radical selected from the group consisting of 2-hydroxyethyl, 3-hydroxy-n-propyl, 2-hydroxy-iso-propyl, 4-hydroxy-n-butyl, 3-hydroxy-isobutyl, 2-hydroxy-tert.-butyl, 5-hydroxy-n-pentyl, 6-hydroxy-n-hexyl, 2-aminoethyl, 3-amino-n-propyl, 2-amino-iso-propyl, 4-amino-n-butyl, 3-amino-isobutyl, 2-amino-tert.-butyl, 5-amino-n-pentyl and 6-amino-n-hexyl radicals.

15. A process according to claim 1, wherein said salt is a salt selected from the group consisting of carbonates, bicarbonates, formates, acetates, oxalates and benzoates.

16. A process according to claim 1, wherein the second distillation is carried out in vacuo under 4 mbar at 160° to 170° C.

* * * * *